US00PP21827P2

(12) United States Plant Patent
van Ruyven

(10) Patent No.: US PP21,827 P2
(45) Date of Patent: Mar. 29, 2011

(54) *CHRYSANTHEMUM* PLANT NAMED 'DELITYCOON'

(50) Latin Name: *Chrysanthemum×morifolium*
Varietal Denomination: Delitycoon

(75) Inventor: Jan van Ruyven, De Lier (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 12/655,765

(22) Filed: Jan. 6, 2010

(51) Int. Cl.
*A01H 5/00* (2006.01)

(52) U.S. Cl. ..... Plt./294

(58) Field of Classification Search ..... Plt./294

See application file for complete search history.

*Primary Examiner*—Annette H Para
(74) *Attorney, Agent, or Firm*—C. A. Whealy

(57) ABSTRACT

A new and distinct cultivar of *Chrysanthemum* plant named 'Delitycoon', characterized by its semi-double-type inflorescences with white-colored ray florets and green-colored disc florets; uniform growth habit; strong and upright flowering stems; freely branching and flowering habit; uniform flowering response; good postproduction longevity; and resistance to *Botrytis*.

2 Drawing Sheets

Botanical designation: *Chrysanthemum×morifolium*.
Cultivar denomination: 'DELITYCOON'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Delitycoon'.

The new *Chrysanthemum* plant is a product of a planned breeding program conducted by the Inventor in De Lier, The Netherlands. The objective of the breeding program is to create new freely flowering semi-double-type *Chrysanthemum* plants with unique ray floret coloration and excellent postproduction longevity.

The new *Chrysanthemum* plant originated from a cross-pollination made by the Inventor in De Lier, The Netherlands in September, 2005 of two unnamed proprietary selections of *Chrysanthemum×morifolium*, not patented. The new *Chrysanthemum* plant was discovered and selected by the Inventor as a single flowering plant from within the progeny of the stated cross-pollination in a controlled greenhouse environment in De Lier, The Netherlands in September, 2006.

Asexual reproduction of the new *Chrysanthemum* plant by terminal cuttings in a controlled greenhouse environment in De Lier, The Netherlands since October, 2006, has shown that the unique features of this new *Chrysanthemum* plant are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Delitycoon'. These characteristics in combination distinguish 'Delitycoon' as a new and distinct cultivar of *Chrysanthemum:*

1. Semi-double-type inflorescences with white-colored ray florets and green-colored disc florets.
2. Uniform growth habit.
3. Strong and upright flowering stems.
4. Freely branching and flowering habit.
5. Uniform flowering response.
6. Good postproduction longevity.
7. Resistant to *Botrytis*.

Plants of the new *Chrysanthemum* are more uniform than plants of the parent selections in growth and flowering habit.

Plants of the new *Chrysanthemum* can be compared to plants of *Chrysanthemum×morifolium* 'Noa', disclosed in U.S. Plant Pat. No. 17,855. In side-by-side comparisons conducted in De Lier, The Netherlands, plants of the new *Chrysanthemum* differed from plants of 'Noa' in the following characteristics:

1. Plants of the new *Chrysanthemum* had longer flowering stems than plants of 'Noa'.
2. Plants of the new *Chrysanthemum* had larger leaves than plants of 'Noa'.
3. Ray florets of plants of the new *Chrysanthemum* were flatter than ray florets of plants of 'Noa'.

Plants of the new *Chrysanthemum* can also be compared to plants of *Chrysanthemum×morifolium* 'Atlantis', disclosed in U.S. Plant Pat. No. 6,074. In side-by-side comparisons conducted in De Lier, The Netherlands, plants of the new *Chrysanthemum* differed from plants of 'Atlantis' in the following characteristics:

1. Plants of the new *Chrysanthemum* had shorter flowering stems than plants of 'Atlantis'.
2. Plants of the new *Chrysanthemum* flowered earlier than plants of 'Atlantis'.
3. Ray florets of plants of the new *Chrysanthemum* were more white in color than ray florets of plants of 'Atlantis'.

4. Plants of the new *Chrysanthemum* were more resistant to *Botrytis* than plants of 'Atlantis'.

BRIEF DESCRIPTION OF THE PHOTOGRAPHS

The accompanying colored photographs illustrate the overall appearance of the new *Chrysanthemum* plant. These photographs show the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Delitycoon' grown as a spray type.

The photograph on the second sheet comprises close-up views of the upper (top of photograph) and lower surfaces (bottom of photograph) of typical inflorescences and leaves of 'Delitycoon'.

DETAILED BOTANICAL DESCRIPTION

The aforementioned photographs and following observations and measurements describe plants grown during the autumn in Maasdijk, The Netherlands, under commercial practice in a glass-covered greenhouse. Plants were initially given 15 days of long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were nine weeks old when the photographs and the description were taken. In the following description, color references are made to The Royal Horticultural Society Colour Chart, 2007 Edition, except where general terms of ordinary dictionary significance are used.

Botanical classification: *Chrysanthemum×morifolium* 'Delitycoon'.

Parentage:

*Female, or seed, parent.*—Unnamed proprietary selection of *Chrysanthemum×morifolium*, not patented.

*Male, or pollen, parent.*—Unnamed proprietary selection of *Chrysanthemum×morifolium*, not patented.

Propagation:

*Type.*—Terminal vegetative cuttings.

*Time to initiate roots, summer.*—About four days at 20° C.

*Time to initiate roots, winter.*—About six days at 20° C.

*Time to produce a rooted young plant, summer.*—About 13 days at 20° C.

*Time to produce a rooted young plant, winter.*—About 15 days at 20° C.

*Root description.*—Fine, fibrous; light brown in color.

*Rooting habit.*—Freely branching, moderately dense.

Plant description:

*Appearance/growth habit.*—Herbaceous semi-double-type cut flower that is typically grown as a spray-type; moderately vigorous growth habit.

*Flowering stem description.*—Aspect: Erect. Length: About 75 cm. Spray diameter: About 28 cm to 30 cm. Diameter: About 6 mm to 7 mm. Lateral branch length: About 10 cm to 15 cm. Internode length: About 2 cm to 2.5 cm. Texture: Pubescent; longitudinally ridged. Color: Close to 146B.

*Foliage description.*—Arrangement: Alternate; simple. Length: About 9 cm to 14 cm. Width: About 5 cm to 9 cm. Apex: Acute. Base: Attenuate. Margin: Palmately lobed, sinuate to dentate; sinuses convergent. Texture, upper and lower surfaces: Pubescent, rough; veins prominent on lower surface. Venation pattern: Pinnate, reticulate. Color: Developing leaves, upper surface: Close to 137B to 137C. Developing leaves, lower surface: Close to 146B. Fully developed leaves, upper surface: Between N137A and 147A; venation, close to 146C. Fully developed leaves, lower surface: Close to 147B; venation, close to 146D. Petiole: Length: About 1 cm to 2.5 cm. Diameter: About 5 mm to 6 mm. Texture, upper and lower surfaces: Pubescent, rough. Color, upper surface: Close to 147C. Color, lower surface: Close to 146C.

Inflorescence description:

*Appearance.*—Semi-double-type inflorescence form with oblong-shaped ray florets; inflorescences borne on terminals, arising from leaf axils; ray and disc florets develop acropetally on a capitulum.

*Fragrance.*—Slightly fragrant.

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering response; plants exposed to 15 days of long day/short night conditions after planting followed by photoinductive short day/long night conditions flower about 45 days later when grown as a spray-type.

*Postproduction longevity.*—In an interior environment, inflorescences and foliage will maintain good color and substance for about three weeks; inflorescences persistent.

*Quantity of inflorescences.*—Freely flowering habit; when grown as a spray type, about 15 to 20 inflorescences develop per flowering stem.

*Inflorescence size.*—Diameter: About 8 cm to 9 cm. Depth (height): About 1.5 cm. Disc diameter: About 1.5 cm. Receptacle height: About 6 mm. Receptacle diameter: About 7 mm. Receptacle color: Close to 145C.

*Inflorescence buds.*—Shape: Oblate. Height: About 4 mm. Diameter: About 7 mm. Color: Close to 153D.

*Ray florets.*—Length: About 3 cm to 4 cm. Width: About 1.5 cm to 2 cm. Shape: Oblong. Apex: Rounded to emarginate. Base: Attenuate. Margin: Entire. Angle: Initially upright to close to perpendicular to the peduncle with development. Texture, upper and lower surfaces: Smooth, glabrous; satiny. Number per inflorescence: About 20 to 25 arranged in about two whorls. Color: When opening, upper and lower surfaces: Close to NN155D. Fully opened, upper and lower surfaces: Close to NN155D.

*Disc florets.*—Shape: Fused tubular, elongated. Apex: Dentate. Length: About 5 mm to 7 mm. Diameter: About 1 mm to 2 mm. Number per inflorescence: About 200, massed at the center. Color, immature: Apex: Close to 145A to 145B. Mid-section: Close to 5A. Base: Close to 145D. Color, mature: Apex: Close to 5B. Mid-section: Close to 145C to 145D. Base: Close to 145D.

*Involucral bracts.*—Length: About 8 mm to 10 mm. Width: About 4 mm to 6 mm. Shape: Ovate. Apex: Rounded. Base: Truncate. Margin: Entire. Texture, upper surface: Smooth, glabrous. Texture, lower surface: Pubescent, slightly rough. Number per inflorescence: About 25 arranged in about two to three whorls. Color, upper surface: Close to 137B. Color, lower surface: Close to 137A.

*Peduncles.*—Length, fourth peduncle: About 10 cm. Length, seventh peduncle: About 12 cm. Diameter: About 2 mm to 3 mm. Angle: About 30° from vertical. Strength: Moderately strong to strong. Texture: Pubescent; longitudinally ridged. Color: More green than 146A.

*Reproductive organs.*—Androecium: Present on disc florets only. Filament length: About 3 mm. Filament color: Close to 145D. Anther length: About 2 mm. Anther color: Close to 15B. Pollen amount: Abundant. Pollen color: Close to 15A. Gynoecium: Present on both ray and disc florets. Style length: About 4 mm to 5 mm. Style color: Light green. Stigma color: Light yellow.

*Seed/fruit.*—Seed and fruit production has not been observed.

Disease/pest resistance: Plants of the new *Chrysanthemum* have been observed to be resistant to *Botrytis*. Plants of the new *Chrysanthemum* have not been observed to resistant to pests and other pathogens common to *Chrysanthemums* grown under commercial conditions.

It is claimed:

1. A new and distinct *Chrysanthemum* plant named 'Delitycoon' as illustrated and described.

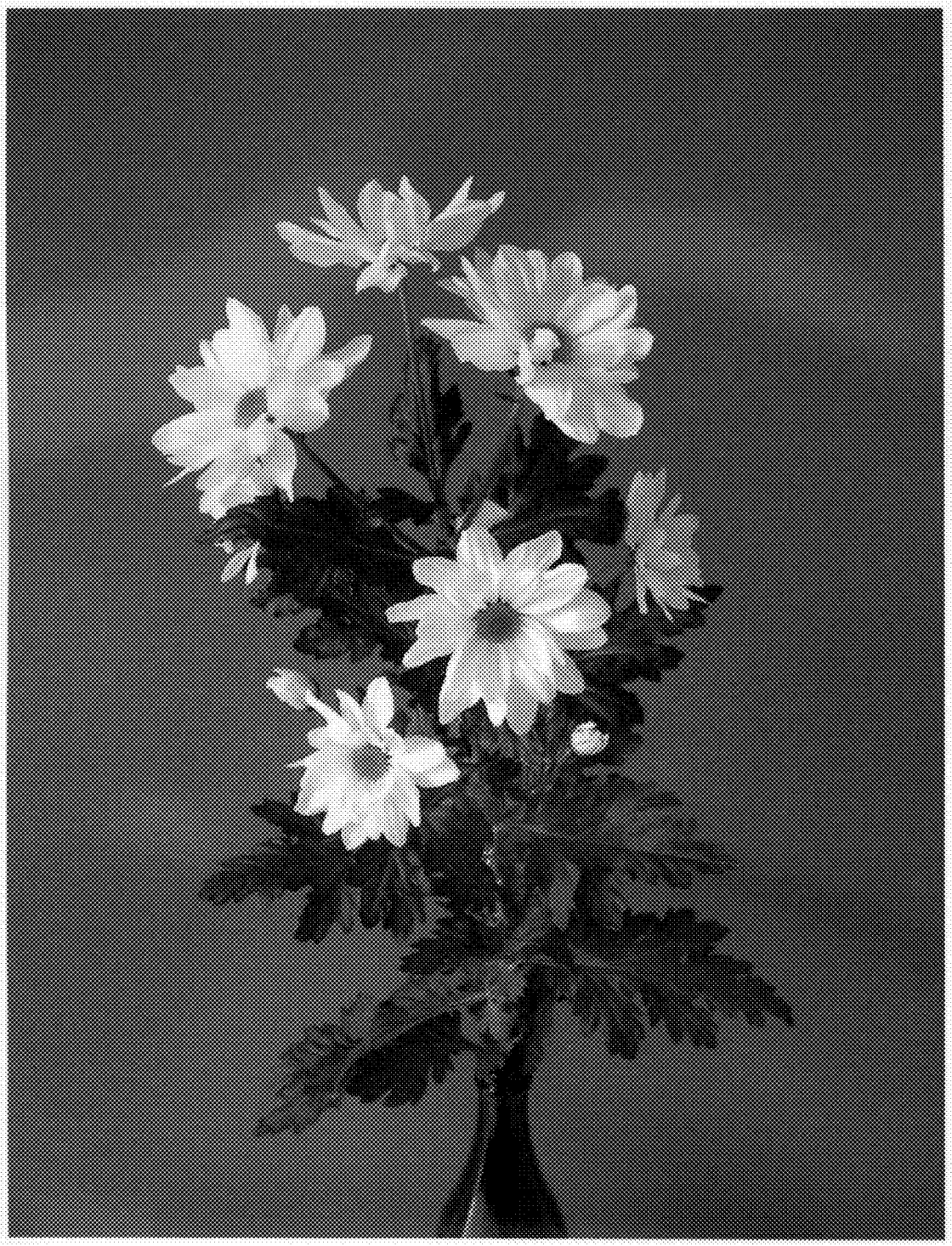

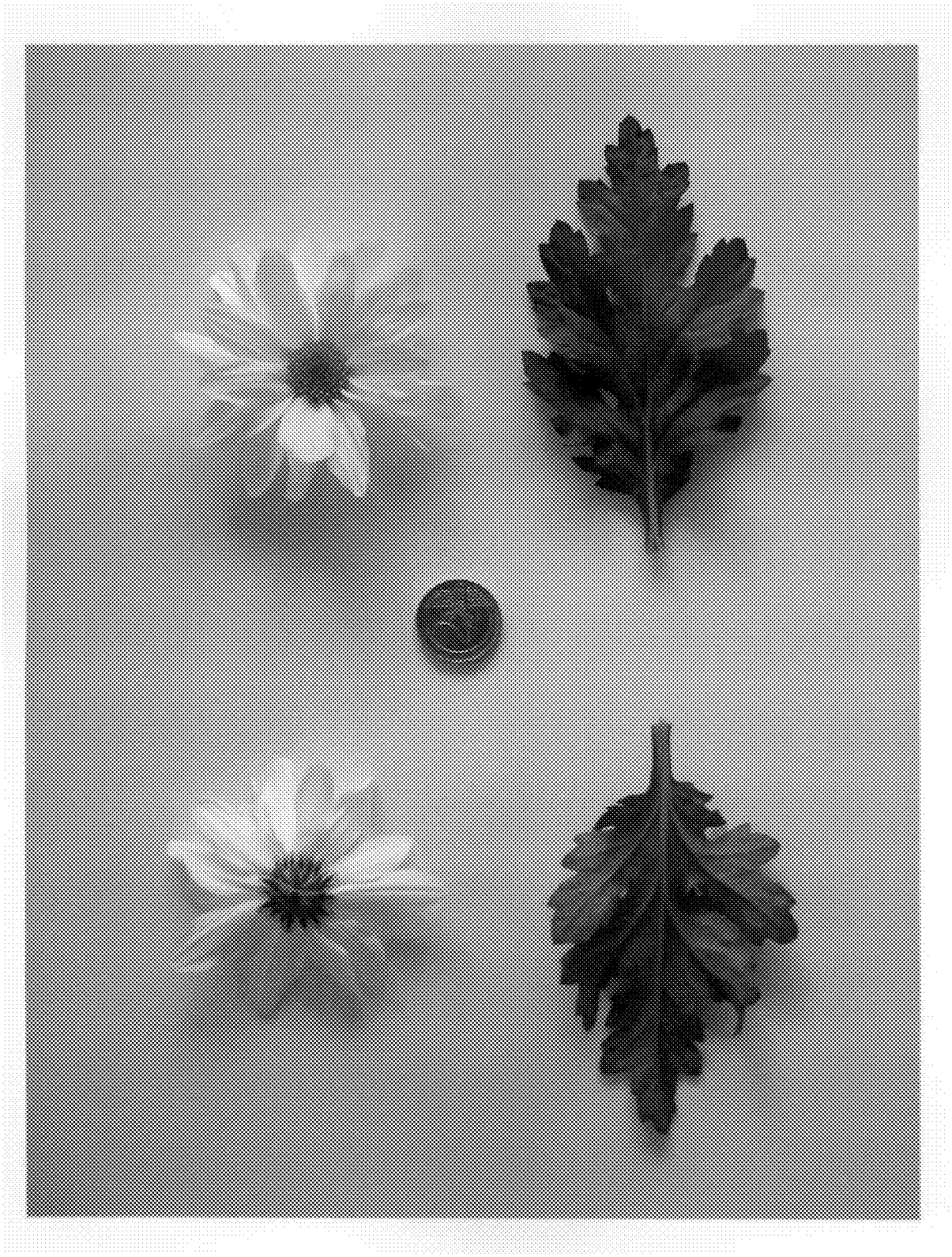

* * * * *